United States Patent
Snyder et al.

(10) Patent No.: US 6,632,239 B2
(45) Date of Patent: Oct. 14, 2003

(54) CONSTRICTION DEVICE INCLUDING REINFORCED SUTURE HOLES

(75) Inventors: Leslie Snyder, Kirkland, WA (US); Joseph R. Pearce, Seattle, WA (US); Martin N. Adams, Seattle, WA (US)

(73) Assignee: Spiration, Inc., Redmond, WA (US)

( * ) Notice: Subject to any disclaimer, the term of this patent is extended or adjusted under 35 U.S.C. 154(b) by 16 days.

(21) Appl. No.: 09/969,949

(22) Filed: Oct. 2, 2001

(65) Prior Publication Data
US 2003/0065339 A1 Apr. 3, 2003

(51) Int. Cl.[7] ............................................. A61B 17/08
(52) U.S. Cl. ...................................... 606/213; 606/151
(58) Field of Search .......................... 606/151–158, 606/191, 141, 203, 213; 29/282; 282/254; 128/844, 899; 602/5, 22, 40, 69; 600/37

(56) References Cited

U.S. PATENT DOCUMENTS

| | | | |
|---|---|---|---|
| 4,881,939 A | | 11/1989 | Newman |
| 5,226,429 A | | 7/1993 | Kuzmak |
| 5,681,271 A | * | 10/1997 | Nelson .......................... 602/27 |
| 5,870,779 A | * | 2/1999 | Heron ........................... 2/403 |
| 6,077,214 A | | 6/2000 | Mortier et al. |
| 6,193,648 B1 | * | 2/2001 | Krueger ......................... 600/37 |
| 6,230,714 B1 | * | 5/2001 | Alferness et al. ............ 128/898 |
| 6,308,709 B1 | * | 10/2001 | Paul ............................. 128/844 |
| 6,425,856 B1 | * | 7/2002 | Shapland et al. .............. 600/37 |

FOREIGN PATENT DOCUMENTS

| | | |
|---|---|---|
| EP | 1 078 601 A2 | 2/2001 |
| FR | 2 773 702 A1 | 1/1998 |
| WO | PCT/US02/31522 | 12/2002 |

\* cited by examiner

*Primary Examiner*—Michael J. Milano
*Assistant Examiner*—Paul A Roberts
(74) *Attorney, Agent, or Firm*—Knobbe, Martens, Olson & Bear, LLP

(57) ABSTRACT

A constriction device that constricts body tissue is configured to be safely sutured to constricted body tissue. The device includes a generally cylindrical elastic sleeve including opposed opened ends and having a wall of substantially uniform thickness that receives body tissue therein to be constricted. The sleeve includes a plurality of suture holes to receive a suture to maintain the sleeve the tissue constricted by the sleeve. The sleeve includes a suture hole reinforcement structure, as for example an increased wall thickness, about each suture hole to permit the device to be sutured to constricted body tissue without damaging the device.

17 Claims, 2 Drawing Sheets

CONSTRICTION DEVICE INCLUDING REINFORCED SUTURE HOLES

BACKGROUND OF THE INVENTION

The present invention is generally directed to a constriction device that constricts body tissue. The present invention is more particularly directed to a constriction device that includes reinforced suture holes to permit a suture to maintain the constriction device from being dislodged from the constricted body tissue while protecting the integrity of the constriction device.

Constriction devices have been contemplated for constricting body tissue. Such devices have been considered for use, for example, in tissue resection procedures and in treating pulmonary disease.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and had increased 33% since 1979.

COPD affects the patient's whole life. It has three main symptoms: cough; breathlessness; and wheeze. At first, breathlessness may be noticed when running for a bus, digging in the garden, or walking up hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, Ipratropium bromide may be indicated. Further, courses of steroids, such as corticosteroids, may be required. Lastly, antibiotics may be required to prevent infections and influenza and pheumococcal vaccines may be routinely administered. Unfortunately, there is no evidence that early, regular use of pharmacotherapy will alter the progression of COPD.

Lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopped remitting for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

The improvements in pulmonary function resulting from LVRS cannot be ignored. However, the surgery is very invasive and fraught with complications. Among the complications is the potential for lung air leaks. Lung tissue is very thin, and fragile hence difficult to suture together. After a lung portion is sectioned and removed, the remaining lung is most often restructured with suture staples. In about thirty percent (30%) of the cases, the difficulty with suturing lung tissue results in air leaks. Treatment for such air leaks depends upon their severity and often, in the most serious cases, requires further open chest surgery.

Air leaks in lungs can be caused by other causes. With increasing age, a patient may develop a weakened section of lung which may then rupture due to an extreme pressure differential, such as may result from simply a hard sneeze. AIDS patients can suffer from air leaks in their lungs. Air leaks in lungs can further be caused by a puncture from a broken rib or a stab wound.

The invention disclosed and claimed in copending U.S. application Ser. No. 09/534,244, incorporated herein by reference, provides an improved therapy for treating COPD and air leaks in lungs. The therapy includes a constriction device which, when deployed on a lung, suppresses air leaks in the lung tissue without requiring any suturing of the effected lung tissue. Still further, by constricting a large enough portion of a lung with the device, lung volume reduction with the concomitant improved pulmonary function may be obtained without the need for any suturing of lung tissue at all.

The lung constriction device includes a jacket or sheath of flexible material configured to cover at least a portion of a lung. The jacket has a pair of opened ends to permit the lung portion to be drawn into the jacket. The jacket is dimensioned to constrict the lung portion after the lung portion is drawn therein. The lung constriction device is preferably formed of expandable, such as elastic, material for receiving the lung tissue while the device is in an expanded or enlarged condition, and then contractible about the lung portion upon release of the expanded condition for constricting the lung tissue.

An important aspect of the device and method disclosed in U.S. application Ser. No. 09/534,244 is the ability to sever the constricting device intermediate its ends. This allows a significant portion of the constricted lung tissue to be removed altogether while permitting a portion of the constricting device to remain in the body for continued suppression of air leaks and maintenance of the remaining lung tissue integrity.

Devices and methods similar to those disclosed in U.S. application Ser. No. 09/534,244 may be employed to advantage in other and different procedures such as in general resection procedures and for body tissue other than lung tissue. Resection procedures are commonly performed for such body tissue as, for example, atrial appendage tissue, ovarian tissue, gall bladder tissue, pancreatic tissue, appendix tissue and spleen tissue. Resection procedures may be required to treat cancer, organ damage, or organ disease, for example.

U.S. application Ser. No. 09/534,244 also discloses and claims various methods and apparatus for deploying the constricting device on body tissue such as lung tissue. One apparatus and method contemplates mechanically expanding the device in a transverse dimension while physically pulling the tissue to be constricted into the device.

Another method contemplates mounting the device over a vacuum chamber and pulling the tissue into the vacuum chamber by engaging the tissue with an opened end of the chamber and then drawing a vacuum in the chamber. This draws the tissue into the chamber. Then, the chamber is withdrawn from the device, leaving the tissue constricted in the device.

A further method contemplates inserting the device into a vacuum chamber and sealing the opened end of the chamber to the device. The opened end of the chamber and the tissue are then brought into sealing engagement. A vacuum is next pulled in the chamber and the device to pull the tissue into the device and chamber. Once the tissue is within the device, the chamber is removed from over the device leaving the tissue constricted in the device.

Although various methods and apparatus have been conceived for effectively deploying constriction devices on body tissue, the constriction devices, over time, may become dislodged due to the nature of the soft tissue on which they are deployed. More specifically, soft body tissue has a tendency to expand at the proximal end of the device causing longitudinal slippage of the device on the body tissue. This may eventually lead to the device slipping totally free from the tissue.

To meet the needs for fixation, U.S. application Ser. No. 09/902,821, filed Jul. 10, 2001, and incorporated herein by reference, discloses and claims a constriction device having positive fixation structure for maintaining the constriction device deployed on the body tissue.

One disclosed device includes a plurality of fixation elements on the inner surface of the sleeve that grasp the body tissue upon release of the sleeve from the expanded condition. More particularly, the fixation elements are adjacent to one of the opposed openings and arranged in a side-by-side relation to grasp the body tissue between adjacent fixation elements when the sleeve is released from the expanded condition. The fixation elements may be integral to the longitudinal side wall or adhered to the inner surface of the sleeve. Still further, the inner surfaces of the fixation elements may have roughened surfaces to further assist in grasping the constricted body tissue.

While the fixation structures disclosed and claimed in the aforementioned U.S. application Ser. No. 09/902,821 are believed to be sufficient alone for maintaining the constriction device on the constricted body tissue, it is contemplated herein that other forms of fixation may be further employed alone or in combination with the above described fixation structures for maintaining the constriction device on the constricted body tissue. One additional form of fixation widely practiced in the medical field is suturing.

While suturing would appear to be an option, simply suturing the constriction device to the constricted body tissue would pose a number of problems. Such problems would arise because the material from which the constriction device is formed is relatively thin elastic material. The suturing of such material could easily cause tearing of the device by the suture. Moreover, the very act of puncturing the device material with a suture needle could readily cause tearing of the device material. Hence, there is a need in the art for a constriction device configured to permit the suturing of the device to constricted body tissue which is structured to protect against the tearing of the device material by either the suture or a suture needle. The present invention addresses that need. the device material by either the suture or a suture needle. The present invention addresses that need.

SUMMARY OF THE INVENTION

The present invention provides a constriction device that constricts body tissue, and which is configured to be sutured to constricted body tissue while protecting the integrity of the device. The device includes an elongated sleeve including at least one opened end and being formed from elastic material to receive, when in an expanded condition, body tissue to be constricted and to constrict the body tissue when released from the expanded condition. The device further includes at least one suture hole that receives a suture to maintain the sleeve on the body tissue and a reinforcement structure about the at least one suture hole.

The reinforcement structure may be an increased thickness of the sleeve about the at least one suture hole. The sleeve may include a plurality of suture holes and the increased thickness may be about each of the suture holes.

Preferably, the suture holes are distributed about the sleeve near to the at least one opened end.

The increased thickness of the sleeve may be formed as a band circumscribing the sleeve with the sutures holes extending through the band. The increased thickness may further have a tapered cross-section for guiding a suture needle into the suture holes. The increased thickness may extend from the inner surface of the sleeve or from the outer surface of the sleeve.

The reinforcement structure may alternatively be a layer of elastic material having a higher tear strength than the elastic material of the sleeve and which is disposed about each of the suture holes. The layer of elastic material may be a continuous band about the sleeve.

In accordance with further aspects, the present invention further provides a constriction device that constricts body tissue. The device includes a generally cylindrical elastic sleeve including opposed opened ends and having a wall of substantially uniform thickness that receives body tissue therein to constrict the body tissue and at least one suture hole to receive a suture to maintain the sleeve on tissue constricted by the sleeve. The sleeve wall has an increased thickness, greater than the substantially uniform thickness, about the at least one suture hole.

The present invention still further provides a constriction device that constricts body tissue, and including sleeve means formed of elastic material including at least one opened end for constricting body tissue received therein, suture hole means for receiving a suture to maintain the sleeve means on the body tissue, and suture hole reinforcing means about the suture hole means for reinforcing the suture hole means.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION

Figure 1:
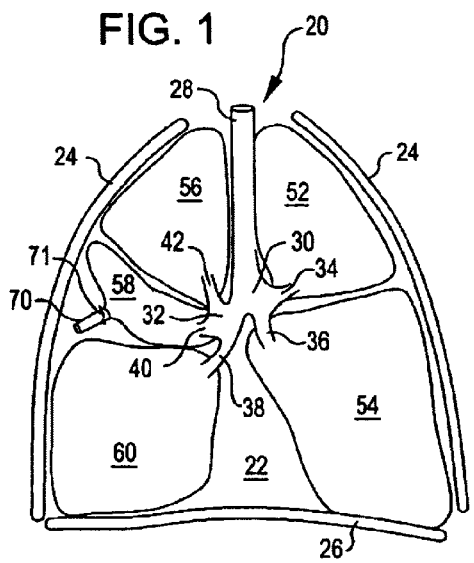
FIG. 1 is a simplified sectional view of a thorax illustrating a respiratory system having a constricting device embodying the present invention deployed on a portion of a lung to effect lung volume reduction.

Referring now to FIG. 1, it is a sectional view of a respiratory system 20. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, and the bronchial branches 34, 36, 38, 40, and 42. The respiratory system 20 further includes left lung lobes 52 and 54 and right lung lobes 56, 58, and 60. Each bronchial branch communicates with a respective different portion of a lung lobe, either the entire lung lobe or a portion thereof.

A healthy respiratory system has an arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air to an inflated condition. When the individual exhales, the diaphragm returns to its original arched condition to decrease the volume of the thorax. The decreased volume of the thorax causes a positive pressure within the thorax which in turn causes exhalation of the lung lobes.

FIG. 1 also shows a constriction device 70 embodying the present invention deployed on lobe 58. The device 70 is configured as a sleeve or sheath formed of a sheet of elastic biocompatible material. The material may be formed from silicone rubber, polyurethane, expanded polytetraflouroethylene, polyester and polyurethane, or nylon and polyurethane, for example. The sleeve is preferably opened at both ends and may be generally cylindrical in configuration.

The sleeve may be applied to the lung lobe while in an expanded condition. This may be accomplished by expanding the sleeve with a vacuum and then pulling the lung portion into the sleeve with the vacuum. When the lung portion is within the sleeve, the expansion of the device is released. With the expansion released, the sleeve is permitted to contract or collapse about the lung portion to constrict the lung portion.

The device 70 may be employed, for example, to suppress air leakages in lungs. It may also find use to advantage in constricting a lung portion suffering from COPD to simulate or achieve lung volume reduction. All of the beneficial effects of lung volume reduction surgery may be realized and, most importantly, without requiring suturing of lung tissue. In accordance with the present invention, the constriction device 70 is fixed on the constricted lung tissue by a suture 71. To that end, the device 70 preferably includes at least one suture hole, and more preferably at least two suture holes. The suture holes are reinforced as will be described subsequently so that when the device is sutured to the lung tissue, neither the suture needle nor the suture tears or adversely affects the integrity of the device 70.

Figure 2:
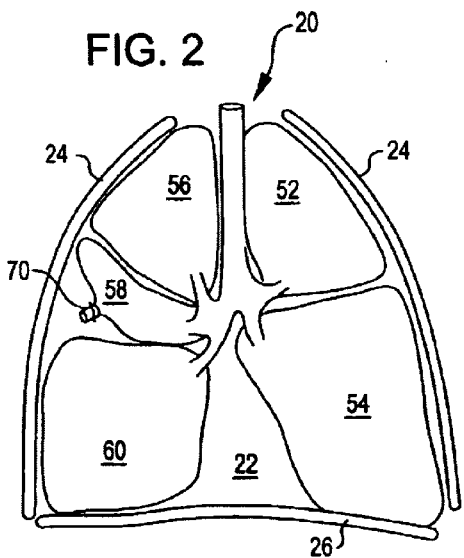
FIG. 2 is a sectional view similar to FIG. 1 but illustrating the respiratory system after the constricted lung portion has been resectioned.

FIG. 2 shows the respiratory system 20 after the constricted lung portion has been resectioned. The device 70 is preferably formed of severable material, such as, any of the materials previously described. This enables the device 70 to be severed or cut intermediate its ends with a suitable bladed instrument to resection the lung lobe 58. The portion of the device 70 remaining on the lobe 58 continues to constrict the lung tissue therein to form an effective seal from leakage. The suture 71 continues to maintain the device 70 on the remaining constricted tissue. Hence, lung volume reduction is rendered an available treatment while negating the need of conventional lung sectioning and avoiding the potentially severe complications which accompany such a procedure.

Figure 3:
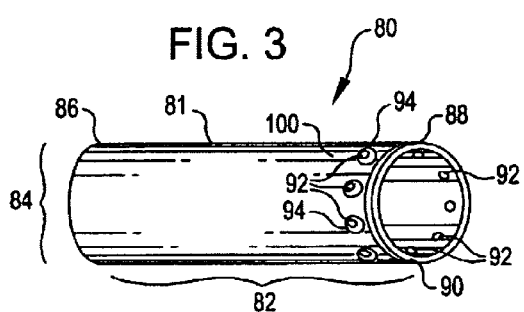
FIG. 3 is a perspective view illustrating a constricting device embodying the present invention.

FIG. 3 illustrates a constriction device 80 embodying the present invention. The device 80 is a generally cylindrical sleeve 81 having a longitudinal dimension 82 and a transverse dimension 84. As previously mentioned, the device 80 is preferably formed of an elastic material permitting the device to expand in the longitudinal dimension and more importantly in the transverse dimension. The device 80 has opposed opened ends 86 and 88. The device may further include at one end, for example, end 88 an integral rim 90.

Figure 4:
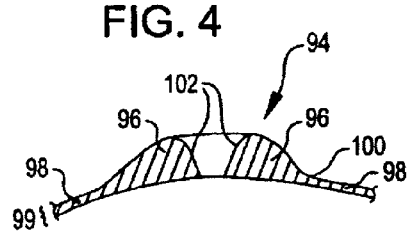
FIG. 4 is a cross-sectional view of a suture hole of the device of FIG. 3 and a suture hole reinforcement structure embodying the present invention.

In accordance with the present invention, the device 80 further includes a plurality of suture holes 92. The suture holes 92 are preferably distributed about the device closely adjacent the opened end 88. As may best be seen in FIG. 4, about each suture hole 92 is a suture hole reinforcement structure 94. In accordance with this embodiment, the suture hole reinforcement structure 94 of each suture hole 92 is an increased thickness or thickened portion 96 in the sleeve wall 98 from the generally uniform thinner wall thickness 99. The increased thickness extends outwardly from the outer surface 100 of the sleeve 81 to define a ring shaped structure about each suture hole 92. As will further be noted in FIG. 4, the reinforcement structure 94 of each suture hole 92 defines a tapered surface 102. The tapered surface serves to help guide a suture needle through its corresponding suture hole.

The suture holes 92 may be preformed so as to initially extend through the sleeve. Alternatively, the suture holes may be defined by the reinforcement structures 94 and more particularly the tapered surfaces 102 without being preformed. This leaves the suture holes to be punched through during the suturing process. However, by virtue of the suture hole reinforcement structures, such punching through can be accomplished safely without damage to the device 80.

Figure 5:
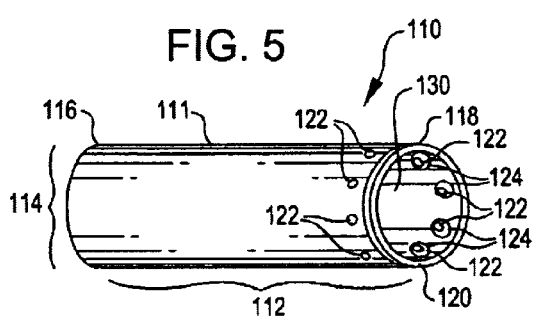
FIG. 5 is a perspective view of another constriction device embodying the present invention.

FIG. 5 illustrates another constriction device 110 embodying the present invention. Again, the device 110 is a generally cylindrical sleeve 111 having a longitudinal dimension 112 and a transverse dimension 110. As previously mentioned, the device 110 is preferably formed of an elastic material permitting the device to expand in the longitudinal dimension and more importantly in the transverse dimension. The device 110 has opposed opened ends 116 and 118 and an integral rim 120 and end 118.

Figure 6:
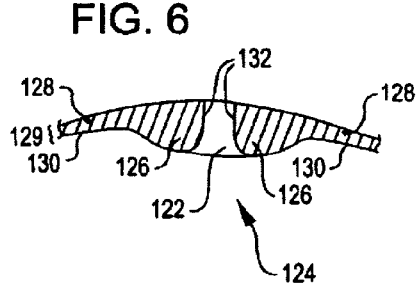
FIG. 6 is a cross-sectional view of a suture hole of the device of FIG. 5 and a suture hole reinforcement structure configured in accordance with another embodiment of the present invention.

Like the device 8 of FIG. 3, the device 110 includes a plurality of suture holes 122 distributed about the sleeve 111 closely adjacent the opened end 118. About each suture hole 122 is a suture hole reinforcement structure 124. As best seen in FIG. 6, each reinforcement structure 124 is an increased thickness or thickened portion 126 in the sleeve wall 128 from the generally uniform wall thickness 129. Here, however, the increased thickness extends inwardly from the inner surface 130 of the sleeve 111 to define a ring shaped structure about each suture hole 122. As will further be noted in FIG. 6, the reinforcement structure 124 of each suture hole 122 defines a tapered surface 132. The tapered surface serves to help guide a suture needle through its corresponding suture hole.

Again the suture holes may be preformed so as to initially extend through the sleeve. Alternatively, the suture holes may be defined by the reinforcement structures without being preformed. While this leaves the suture holes to be punched through during the suturing process, however, such punching through can be accomplished safely without damage to the device by virtue of the suture hole reinforcement structures.

Figure 7:
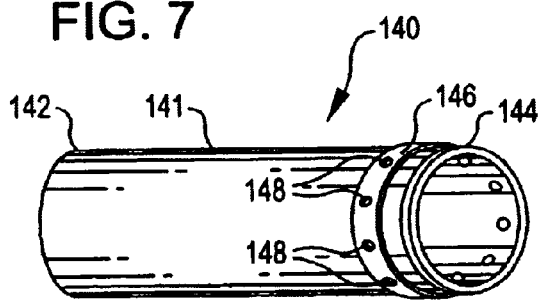
FIG. 7 is a perspective view of another constriction device embodying the present invention.
Figure 8:
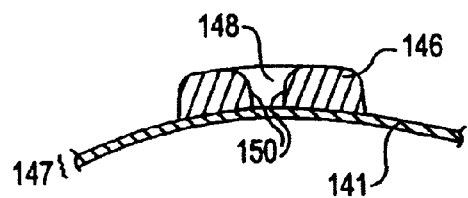
FIG. 8 is a cross-sectional view of a suture hole of the constriction device of FIG. 7 and illustrating its reinforcing structure in accordance with a still further embodiment of the present invention.

FIGS. 7 and 8 illustrate another constriction device 140 embodying the present invention. The device 140 again is a generally cylindrical sleeve 141 having opposed opened ends 142 and 144. Adjacent the opened end 144 and extending about the sleeve is a continuous band 146. The band 146 may be a thickened portion of the sleeve from its substantially uniform thickness 147 or preferably is an additional layer of elastic material but having a higher tear resistance than the material forming the sleeve 141 that is bonded to the sleeve 141. The band includes a plurality of apertures 148 defining suture holes for the sleeve 141. The apertures 148 include tapered surfaces 150 to guide a suture needle through the apertures and the sleeve. The suture holes are thus reinforced by the band 146 against tearing or the like by the suture or suture needle. Here, however, the wall thickness of the sleeve 141 must be punched through by the suture needle passing through the suture holes 148.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A constriction device that constricts body tissue, the device comprising:

an implantable elongated sleeve including at least one opened end and being formed from elastic material to receive, when in an expanded condition, internal body tissue to be constricted and to constrict the internal body tissue when released from the expanded condition;

at least one suture hole that receives a suture to maintain the sleeve on the internal body tissue; and a reinforcement structure being an increased thickness of the elastic material of the sleeve about the at least one suture hole.

2. The device of claim 1 wherein the sleeve includes a plurality of suture holes and wherein the reinforcement structure is an increased thickness of the elastic material about each of the suture holes.

3. The device of claim 2 therein the suture holes are distributed about the sleeve.

4. The device of claim 2 wherein the suture holes are distributed about the sleeve near to the at least one opened end.

5. The device of claim 1 wherein the reinforcement structure includes a tapered cross-section that guides a suture needle into the at least one suture hole.

6. The device of claim 1 wherein the sleeve has an inner surface and wherein the increased thickness extends from the inner surface of the sleeve.

7. A constriction device that constricts internal body tissue, the device comprising:

an implantable generally cylindrical elastic sleeve including opposed opened ends and having a wall of substantially uniform thickness that receives the internal body tissue therein to constrict the internal body tissue; and at least one suture hole that receives a suture to maintain the sleeve on the internal body tissue constricted by the sleeve, the sleeve wall thickness about the at least one suture hole being greater than the substantially uniform thickness.

8. The device of claim 7 wherein the sleeve includes a plurality of suture holes, and the sleeve wall thickness about each suture hole being greater than the substantially uniform thickness.

9. The device of claim 8 wherein the suture holes are distributed about the sleeve.

10. The device of claim 8 wherein the suture holes are distributed about the sleeve near one of the opposed opened ends.

11. The device of claim 7 wherein the at least one suture hole includes a tapered cross-section that guides a suture needle into the at least one suture hole.

12. An implantable constriction device that constricts body tissue, the device comprising:

implantable sleeve means formed of elastic material including at least one opened end for constricting internal body tissue received therein;

suture hole means for receiving a suture to maintain the sleeve means on the internal body tissue; and means for reinforcing the suture hole means being formed of the elastic material about the suture hole means.

13. The device of claim 12 wherein the device includes a plurality of suture hole means, and the reinforcing means being formed of the elastic material about each of the suture hole means.

14. The device of claim 13 wherein the suture hole means are distributed about the sleeve.

15. The device of claim 13 wherein the suture hole means are distributed about the sleeve near to the at least one opened end.

16. The device of claim 12 wherein the suture hole means includes a tapered cross-sections that guides a suture needle into the suture hole means.

17. The device of claim 12 wherein the sleeve means has an inner surfaces, and the reinforcing means includes an increased thickness that extends from the inner surface of the sleeve means.

* * * * *